United States Patent [19]

Benneche et al.

[11] Patent Number: 4,478,839
[45] Date of Patent: Oct. 23, 1984

[54] SUBSTITUTED PYRIMID-2-ONES, THE SALTS THEREOF, PROCESSES FOR THEIR PREPARATION AND PHARMACEUTICAL COMPOSITIONS CONTAINING THEM

[75] Inventors: Tore Benneche; Mikkel Gacek; Kjell Undheim, all of Oslo, Norway

[73] Assignee: Nyegaard & Co. A/S, Oslo, Norway

[21] Appl. No.: 416,670

[22] Filed: Sep. 10, 1982

[30] Foreign Application Priority Data

Sep. 11, 1981 [GB] United Kingdom ............... 8127505

[51] Int. Cl.$^3$ ................. C07D 239/36; A61K 31/505
[52] U.S. Cl. .................................... 424/251; 544/316
[58] Field of Search ......................... 544/316; 424/251

[56] References Cited

U.S. PATENT DOCUMENTS 4,052,400 10/1977 Schwam .......................... 260/256.4
4,395,406 7/1983 Gacek ................................. 424/180

FOREIGN PATENT DOCUMENTS 1561290 2/1980 United Kingdom ................ 424/251

OTHER PUBLICATIONS

March, Advanced Organic Chemistry, p. 823 (1977).
Japanese Abstracts, vol. 1, No. 120, dated Oct. 12, 1977, p. 2695 C 77.

Primary Examiner—Robert Gerstl
Attorney, Agent, or Firm—Bacon & Thomas

[57] ABSTRACT

Compounds of general formula:

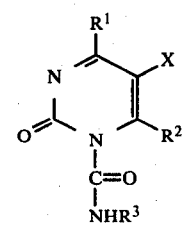

(wherein X represents a halogen atom or a trifluoromethyl group; $R^1$ and $R^2$, which may be the same or different, each represents a hydrogen atom, or a $C_{1-4}$ alkyl group, and $R^3$ represents a hydrogen atom or a $C_{1-5}$ saturated or unsaturated, straight or branched acyclic aliphatic group; a $C_{3-8}$ saturated or unsaturated cyclic aliphatic group; a heterocyclic substituted aliphatic group; an araliphatic group; or a heterocyclic or carbocyclic aryl group; any of said groups optionally carrying one or more substituents selected from halogen, oxo, hydroxy, mercapto, $C_{1-4}$ alkyl, $C_{1-4}$ alkoxy, $C_{1-4}$ alkanoyloxy and amino) and, where an acidic or basic group is present, physiologically compatible salts thereof have been found to be of use in combating abnormal cell proliferation.

The compounds of formula I may be prepared by reaction of a 5-halo- or 5-trifluoromethyl-pyrimidin-2-one with an appropriate isocyanate.

9 Claims, No Drawings

SUBSTITUTED PYRIMID-2-ONES, THE SALTS THEREOF, PROCESSES FOR THEIR PREPARATION AND PHARMACEUTICAL COMPOSITIONS CONTAINING THEM

The present invention relates to 1-carbamoyl derivatives of pyrimidin-2-ones having interesting physiological activity, pharmaceutical compositions containing them, processes for their preparation and their use as medicaments.

Abnormal cell proliferation is the basic cause of a number of diseases such as cancers, leukaemias, cutaneous cellular proliferation, e.g. contact dermatitis or psoriasis, or auto-immune diseases where proliferation of lymphocytes leads to an undesirable immune response against some of the normal tissues of the body.

The present invention is based on the discovery that compounds of the formula:

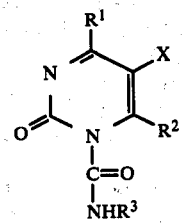

(I)

(wherein X represents a halogen atom or a trifluoromethyl group; $R^1$ and $R^2$, which may be the same or different, each represents a hydrogen atom, or a $C_{1-4}$ alkyl group, and $R^3$ represents a hydrogen atom or a $C_{1-5}$ saturated or unsaturated, straight or branched acyclic aliphatic group; a $C_{3-8}$ saturated or unsaturated cyclic aliphatic group; a heterocyclic substituted aliphatic group; an araliphatic group; or a heterocyclic or carbocyclic aryl group; any of said groups optionally carrying one or more substituents selected from halogen, oxo, hydroxy, mercapto, $C_{1-4}$ alkyl, $C_{1-4}$ alkoxy, $C_{1-4}$ alkanoyloxy and amino) and, where an acidic or basic group is present, the salts thereof possess the ability to inhibit cell proliferation.

Abnormal cell proliferation can be combated by administration of a drug which irreversibly interferes with cell-division. Such drugs are generally only able to attack the cells during a particular phase of the cell cycle, for example the S-phase during which DNA is synthesised. Although the drug cannot distinguish between abnormal and normal cells which are in the phase susceptible to attack, use can be made of the fact that a significant proportion of normal cells, e.g. bone marrow, are in a resting phase for relatively long periods and do not enter the susceptible phase while the drug is present. These latter cells provide a reservoir of healthy normal cells whch eventually resume cell division even though a large number of normal cells have been irreversibly damaged by the drug. On the other hand, the abnormal cells such as tumour cells, generally tend not to have a large reservoir of resting cells and cycle more slowly and consequently when the drug has been eliminated from the system, there are fewer cells capable of dividing. If a second dose of the drug is administered when the normal cells have recovered their usual numbers but the abnormal cells are still depleted, this process can be repeated and the number of abnormal cells still further reduced. By a series of carefully timed doses of the drug, it is often possible to eliminate the abnormal cells.

Another way in which such a drug can be used to combat abnormal cell proliferation, is to administer a preliminary drug which acts to arrest reversibly the cycle of cell division in a particular phase, for example the metaphase, so that when the drug has been eliminated from the system, all the cells resume division synchronously. However, the cell division cycle of the abnormal cells will generally be different from that of the normal cells, and a time can be selected at which the abnormal cells are susceptible to attack by the irreversibly acting drug while the normal cells are in a resistant phase.

The compounds of the present invention inhibit DNA synthesis and are thus particularly useful in combating abnormal cell proliferation.

Preferred $C_{1-5}$ saturated or unsaturated, straight or branched aliphatic acyclic groups are $C_{1-3}$ alkyl groups and alkenyl or alkynyl groups containing 3 or more carbon atoms. The term "$C_{3-8}$ saturated or unsaturated cyclic aliphatic group" preferably refers to $C_{3-8}$ cycloalkyl or -alkenyl groups.

The term "heterocyclic" as used herein preferably relates to groups having 5 or 6 ring members and having one or more, e.g. one heteroatom(s) selected from oxygen, nitrogen or sulfur and optionally carrying a fused ring. The ring systems may, unless otherwise stated, be saturated or unsaturated, e.g. aromatic. The term thus extends inter alia, to saccharide residues, i.e. glycosyl groups, for example, furanosyl and pyranosyl derivatives e.g. glucofuranone derivatives, including deoxy derivatives thereof, as well as aromatic heterocyclic rings such as pyridyl or thienyl groups e.g. pyrid-3-yl or thien-2-yl groups.

The term "carbocyclic aryl" as used herein relates, for example, to aromatic ring systems with up to 10 carbon atoms e.g. phenyl or naphthyl optionally carrying substituents as indicated above.

The term "araliphatic" as used herein relates, for example, to aralkyl groups with up to 4 carbon atoms in the alkyl portion and with up to 10 carbon atoms in the aryl portion. Thus, for example, the aryl portion may be a phenyl or naphthyl group optionally carrying one or more substituents as indicated above. Thus for example $R^3$ may represent a benzyl group optionally carrying one or more halogen atoms e.g. chlorine. Similarly, heterocyclic substituted aliphatic groups preferably possess 1-4 carbon atoms in the aliphatic portion.

It will also be appreciated that the substituents listed above may, if desired, be present simultaneously and in combination where appropriate. Thus, for example, a carbon atoms on a $C_{1-4}$ alkyl substituent on a ring system as described above or a carbon atoms of a $C_{1-5}$ saturated or unsaturated cyclic aliphatic group may carry an oxo group as well as a hydroxy, $C_{1-4}$ alkoxy or amino group thus resulting in the presence of a carboxy, esterified carboxy or amido group. Similarly for example such a carbon atom or carbon atoms may carry halogen atom(s) e.g. fluorine atoms, thus resulting in the presence of, for example, perfluorinated alkyl groups.

Compounds of formula I containing solubilising groups are of particular interest. Such compounds include, for example, polyhydroxy containing groups such as groups derived from carbohydrates, amino acids and hydroxy acids.

Advantageously $R^3$ represents a $C_{7-14}$ aralkyl group, a $C_{6-10}$ carbocyclic aryl group, a 5- or 6- membered heterocyclic aryl substituted $C_{1-3}$ alkyl group, a 5- or 6- membered heterocyclic aryl group or a $C_{1-5}$ alkyl or alkenyl group, said groups optionally carrying one or more, e.g. one, substituents selected from $C_{1-4}$ alkyl and halogen. Such substituents may therefore include for example, chlorine or $C_{1-4}$ haloalkyl such as trifluoromethyl. $R^3$ preferably represents a benzyl, phenyl, naphthyl, thienylmethyl, pyridyl or $C_{1-3}$ alkyl or alkenyl group optionally carrying one or more, e.g. one, substituents selected from $C_{1-4}$ alkyl and halogen e.g. chlorine or trifluoromethyl substituents. Thus $R^3$ especially represents a methyl, 2-chloroethyl, allyl, chlorobenzyl (e.g. 4-chlorobenzyl), phenyl, trifluoromethylphenyl (e.g. 4-trifluoromethylphenyl), naphthyl, thienylmethyl or pyridyl group, methyl being particularly preferred.

Preferably only one of $R^1$ and $R^2$ is other than hydrogen and more preferably both of $R^1$ and $R^2$ are hydrogen.

The group X in the compounds of formula I is preferably fluorine, chlorine, bromine or iodine, more particularly chlorine.

Preferred compounds of the present invention include:

1-methylcarbamoyl-5-bromopyrimidin-2-one and, in particular, 1-methylcarbamoyl-5-chloropyrimidin-2-one.

Salts of the compounds of formula I may include salts with alkali metal or alkaline earth metals e.g. sodium, potassium, magnesium or calcium or ammonium (including substituted ammonium) salts. Compounds according to the invention carrying hydroxyl or amino groups also in general, possess enhanced water solubility, the latter of course forming acid addition salts e.g. with mineral acids such as hydrochloric acid or sulphuric acid or organic acids such as acetic, tartaric or citric acid. However, in general non-ionic compounds of the invention are preferred. It will be appreciated that the salts of the compounds of formula I for use in pharmaceutical compositions are physiologically compatible salts. Other salts may however be useful in the preparation of the compounds of formula I and the physiologically compatible salts thereof.

It will be appreciated that certain of the compounds of formula I will exist in geometrically or optically active isomeric forms. The present invention extends to cover all of these isomeric forms and mixtures thereof.

The compounds of formula I as hereinbefore defined may, for example, be prepared by the following process which constitutes a further feature of the present invention:

The reaction of a compound of the formula:

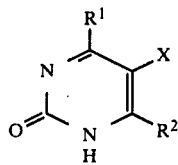
(II)

(wherein $R^1$, $R^2$ and X are as hereinbefore defined) or a salt thereof with a compound of the formula $$R^{3'}-N=C=O \qquad (III)$$

(wherein $R^{3'}$ is as hereinbefore defined for $R^3$ or is a group convertible thereto) whereby a compound of formula I is obtained.

Where $R^3$ is intended to include hydroxyl or other groups which may be reactive with the —NCO grouping, these can be in protected form in $R^{3'}$, for example by formation of acyl or silyl derivatives.

Where it is desired to use a salt of the compound of formula II the salt is advantageously a metal salt e.g. an alkali metal or an alkaline earth metal salt or an ammonium salt.

The reaction may be effected in the presence of any convenient solvent, for example pyridine, nitromethane, dimethylsulfoxide, N,N-dimethylformamide N,N-dimethylacetamide, dioxan, diglyme or dichloromethane. It may be advantageous to effect the reaction in the presence of pyridine, in the preparation of compounds of formula I in which $R^3$ represents a phenyl or pyridyl group. The choice of optimal solvent can readily be determined by experiment. The reaction is conveniently effected at a temperature of from ambient temperature to the boiling temperature of the reaction mixture, advantageously at an elevated temperature e.g. 90°-100° C. or at the boiling point for a lower boiling solvent. The preferred molar ratio of isocyanate to pyrimidin-2-one is about 1.5. Moreover the reaction may if desired be effected in the presence of an organic base, e.g. triethylamine, triethylenediamine or DBU(1,8-diazabicyclo[5.4.0]undecene-7), which serves as a catalyst for the reaction.

The compounds of formula II used as starting materials in the above-mentioned process may, for example, be prepared as described in our British Pat. No. 1,561,290. It is, however, difficult to prepare a 5-trifluoromethylpyrimidin-2-one of formula II by introduction of a trifluoromethyl group into the pyrimidin-2-one ring while direct ring closure methods are generally rather inefficient. The process described hereinafter enables a 5-trifluoromethylpyrimidin-2-one of formula II to be prepared in good yield by hydrolysis of a compound of the formula:

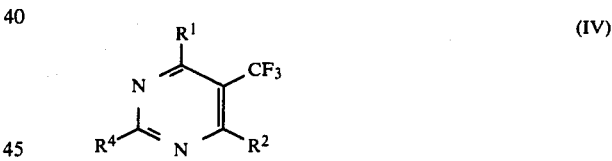
(IV)

(wherein $R^1$ and $R^2$ are as herein defined and $R^4$ represents a halogen atom or a group —$SR^5$, $SOR^5$, or —$SO_2R^5$ in which $R^5$ represents a hydrocarbyl group such as a $C_{1-32}$ saturated or unsaturated, straight or branched, cyclic or acylic aliphatic group or an araliphatic or heterocyclic substituted aliphatic group, a heterocyclic group or an aryl group which groups may if desired carry one or more substituents selected from halogen atoms and oxo, nitro, hydroxy, etherified hydroxy, esterified hydroxy, primary, secondary or tertiary amino, acylamino, etherified mercapto or —SO or —$SO_2$ derivatives thereof and esterified phosphonic acid groups (and where an acidic or basic group is present, the salts thereof.

The process is preferably effected by the use of a sulfone of formula IV in which R represents the group —$SO_2R^5$ wherein $R^5$ is as hereinbefore defined.

The sulphones of formula IV may be obtained, as described hereinafter, from a known compound 2-chloro-5-trifluoromethylpyrimidine.

Analogues of the sulfones of formula IV having a halogen atom in the 5-position of the pyrimidine ring have been described in detail in our European Patent Application No. 81300098.1 (Publication No. 33195) and preferred definitions of the group $R^4$ in formula IV above are given in detail in relation to the group $R^3$ in formula I in our above-mentioned European Patent Application. A compound of formula IV herein is preferably used however in which $R^5$ represents an alkyl e.g. lower alkyl group (for example with 1 to 6 carbon atoms) such as an ethyl or methyl group.

The hydrolysis of the compounds of formula IV as hereinbefore defined is conveniently effected by the use of a base such as an alkali metal hydroxide e.g. sodium or potassium hydroxide. The hydrolysis is conveniently effected at a temperature within the range 0° to 30° C. e.g. at ambient temperature.

The sulphone of formula IV is conveniently prepared by a method analogous to that described in our European Patent Application No. 81300098.1 (Publication No. 33195). Thus for example the compound of formula IV may be prepared by oxidation of the corresponding sulphide of the formula:

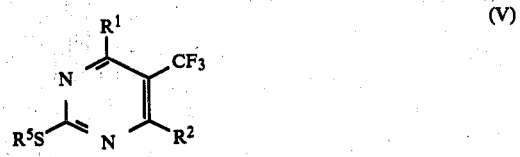

(wherein $R^1$, and $R^2$ and $R^5$ are as hereinbefore defined) by any convenient method including the use of (1) a manganese oxidising agent, for example a permanganate preferably potassium permanganate, conveniently in the presence of an acid e.g. acetic acid; (2) the use of chlorine or a hypochlorite e.g. sodium hypochlorite in an aqueous solution of the sulfide or sulfoxide; or (3) the use of a peroxide or peracid oxidising system such as hydrogen peroxide conveniently in the presence of an acid e.g. acetic acid advantageously at ambient temperature, or more preferably, m-chloroperbenzoic acid conveniently in the presence of a solvent e.g. dichloromethane and advantageously at a temperature from $-30°$ C. to $+30°$ C. conveniently at ambient temperature, or the use of molybdenum peroxide conveniently in the presence of water and/or hexamethyl-phosphoramide.

The compound of formula V is conveniently prepared by reaction of a compound of formula:

(wherein $R^1$ and $R^2$ are as hereinbefore defined and Y represents a leaving atom or group) with a thiol of the formula $R^5SH$ or a thiolate of the formula

(wherein $R^5$ is as hereinbefore defined, M represents the stabilising cation and n represents the charge on the cation) whereby a compound of formula I in which n is 0 is obtained.

The reaction of the compound of formula VI with the compound of formula VII is conveniently effected by the use of a compound of formula VI in which Y represents a halogen atom e.g. a chlorine or bromine atom. The reaction is a nucleophilic substitution reaction, the nucleophile being in the form $R^5S-$ and thus where the compound of formula VII is used in the form of a thiol, the reaction is preferably effected in the presence of a base sufficiently strong to remove the thiol proton to give the aforementioned nucleophile. Preferred bases include alkoxides, for example alkali metal and alkaline earth metal alkoxides such as sodium or potassium alkoxides e.g. ethoxides. The reaction is conveniently effected at an elevated temperature preferably at the reflux temperature of the reaction mixture.

The compound of formula VI has been described by A. Serban et al (German OLS No. 2,820,032).

According to a further feature of the present invention there are provided pharmaceutical compositions comprising as active ingredient at least one compound of formula I, or a physiologically compatible salt thereof as hereinbefore defined in association with a pharmaceutical carrier or excipient.

It will be appreciated that the term "pharmaceutical composition" as used herein includes veterinary compositions.

The compositions may be formulated for pharmaceutical administration in any suitable manner. Thus, compositions will normally be in a form suitable for oral or parenteral administration, such as tablets, coated tablets, capsules, granulates and solutions, for ingestion by the gastrointestinal tract, or sterile injectable solutions in pyrogen free water. The compositions will generally be administered at a daily dose level in the range 0.5 to 5.0 g of the compound of the invention; the composition will conveniently be formulated in dosage units, each dosage unit typically containing from 100 mg to 1.0 g of the compound of the invention, though units containing as much as 5 g may occasionally be suitable.

Conventional carrier and excipient ingredients may be used, such as talc, gum arabic, lactose, starch, magnesium stearate, cocoa butter, animal and vegetable fats, paraffin derivatives, propellants, and various wetting, dispersion, emulsifying, flavouring and preserving agents.

The compositions of the invention may be formulated together with other chemotherapeutic agents, for example, cytosine arabinoside. This has been found a good partner in view of the combined effect the two ingredients have on the cell growth pattern. Other chemotherapeutic agents which may, for example be used as ingredients in the pharmaceutical compositions of the present invention include vincristine or vinblastine.

According to a still further feature of the present invention there is provided a method of combating abnormal cell proliferation in a host which comprises administering to said host an effective amount of a compound of formula I as hereinbefore defined, or where an acidic or basic group is present, a physiologically compatible salt thereof.

The following Examples are provided by way of illustration only:

EXAMPLE 1

1-N-Methylcarbamoyl-5-fluoropyrimidin-2-one

Methylisocyanate (3.8 mmol) was added dropwise with vigorous stirring to a solution of 5-fluoropyrimidin-2-one (described in Undheim K. and Gacek M. Acta. Chem. Scand 23 (1969) 294) (2.5 mmol) in anhydrous DMSO (3.2 ml). The exothermic reaction started at once and a white solid was precipitated. The precipitate was collected after 50 minutes, washed with a little water, sucked dry, washed with ethyl acetate and dried; yield 60%, m.p. 166° C., $^1$H NMR (CDCl$_3$): δ3.03 (N-Me), 8.66 (H-4), 8.71 (H-6).

EXAMPLE 2

1-N-Methylcarbamoyl-5-chloropyrimidin-2-one

The title compound was prepared as described in Example 1 from 5-chloropyrimidin-2-one (described in Crosby G. and Berthold V. R. J. Org. Chem. 25 (1960) 1916) in 74% yield, m.p. 233° C. $^1$N NMR (CDCl$_3$): δ3.03 (NMe), 8.60 (H-4), 8.80 (H-6).

EXAMPLE 3

1-N-Methylcarbamoyl-5-chloropyrimidin-2-one

Methyl isocyanate (56.5 ml) was added dropwise over 15 minutes, with cooling, to a stirred solution of 5-chloropyrimidin-2-one (25 g) in N,N-dimethylformamide (290 ml) and triethylamine (30.4 ml). The temperature of the reaction mixture was kept at approximately 22° C. The mixture was stirred at room temperature for a further 40 minutes and then cooled in an ice bath. The solid was collected, washed with cold dichloromethane (4×215 ml), briefly air dried and then dried in vacuo at room temperature to give the title compound as white crystals (33.36 g), m.p. 241°–243° C. decomp. U.V. data: $\lambda_{max}$ EtOH 230 nm (ε10,370), 322.5 mm (ε1,700).

EXAMPLE 4

1-N-Methylcarbamoyl-5-bromopyrimidin-2-one

The title compound was prepared as described in Example 1 from 5-bromopyrimidin-2-one (described in Tee S. O. and Banergee S. Canad. J. Chem. 52 (1974) 451) in 67% yield, m.p. 236°–238° C. $^1$H NMR (CDCl$_3$): δ3.03, 8.68 (H-4), 8.91 (H-6).

EXAMPLE 5

1-Allylcarbamoyl-5-bromopyrimidin-2-one

A mixture of 5-bromopyrimidin-2-one (2 mmol) and allylisocyanate (3 mmol) in dimethyl formamide (2 ml) was stirred together at room temperature until a clear solution resulted (ca. 3 h) before the solvent was distilled off at 1 mmHg, the residue triturated with ether and then with water; the residue was the title compound, yield 59%. MS (70 eV) m/e: 257/255 (M,O), 176 (31), 174 (33), 148 (9), 106 (8), 104 (8), 95 (60), 83 (20), 56 (100).

EXAMPLE 6

1-(2-Chloroethyl)carbamoyl-5-chloropyrimidin-2-one was prepared from 5-chloropyrimidin-2-one and 2-chloroethylisocyanate in dimethyl formamide as described above; yield 40%. $^1$H NMR (DMSO-d$_6$): δ3.6 (CH$_2$CH$_2$, broad m), 8.41 (2H-4,6), 9.5 (NH).

EXAMPLE 7

1-N-Methylcarbamoyl-5-iodopyrimidin-2-one

The reaction was carried out as above on 5-iodopyrimidin-2-one (described in Arantz, B. W. and Brown D. J. J. Chem. Soc. (1971)1889) (4 mmol) and methylisocyanate (16 mmol) in anhydrous DMSO (0.5 g). The precipitate was collected after stirring for 90 min at room temperature, and washed with ether; yield 85%, m.p. >260° C. (dec.). $^1$H NMR (DMSO-d): δ2.96 (N-Me), 8.30 (H-4), 8.66 (H-6).

EXAMPLE 8

1-N-(4-Chlorobenzyl)carbamoyl-5-bromopyrimidin-2-one

The reaction was carried out as above on 5-bromopyrimidin-2-one (3.5 mmol) and 4-chlorobenzylisocyanate (6 mmol) in DMSO (0.3 g). The reaction was run at 50° C. for 40 min, the precipitate filtered off from the reaction mixture and washed with ether; yield 59%, m.p. 158°–160° C. $^1$H NMR (DMSO-d$_6$): δ4.41 (N-C$\underline{H}_2$), 7.30 (Ph), 8.38 (H-4 and H-6).

EXAMPLE 9

1-N-(2-Thienyl)methylcarbamoyl-5-bromopyrimidin-2-one

2-Chloromethylthiophene (75.4 mmol) and silver isocyanate (75.4 mmol) were stirred together in ether (100 ml) at room temperature for 24 h. Over the next 24 h additional silver isocyanate was added at intervals (2.5 g×3; 50.1 mmol) to the stirred mixture. Then the mixture was filtered, the filtrate evaporated and the residual oil distilled; b.p. 78°–80° C. 38 mmHg, yield of (2-thienyl)methyl isocyanate 2.6 g (25%). $^1$H NMR (CDCl$_3$): δ4.58 (CH$_2$), 6.9–7.3 (3H-3,4,5). IR (film): 2250 cm$^{-1}$ (NCO).

(2-(Thienyl)methylisocyanate (1.7 mmol) as prepared above was added to 5-bromopyrimidin-2-one (1.0 mmol) in DMSO (0.10 g) and the mixture was stirred at 50° C. for 40 min. The cold reaction mixture was then triturated with ether and then with acetone; the residual material which is the title product was obtained in 50% yield (0.17 g), decomp. from ca. 120° C.

$^1$H NMR (DMSO-d$_6$): δ4.4 (CH$_2$), 6.8–7.6 (thiophene), 8.42 (H-4 and H-6).
IR (KBr): 1730 cm$^{-1}$ (CONHCH$_2$C$_4$H$_3$S), 1665 cm$^{-1}$ (CO).

EXAMPLE 10

1-(N-3-Pyridylcarbamoyl)-5-bromopyrimidin-2-one

A mixture of 5-bromopyrimidin-2-one (0.18 g 1.0 mmol) and 3-pyridyl isocyanate [see Hyder S. and Wilbert, G.: Chem. & Ind. (1967) 1406] (3.0 mmol) in pyridine (1.0 ml) was stirred at 65° C. until a clear solution results (ca. 5 min). The mixture was then stirred at room temperature for 20 min before the precipitate was collected and washed with ether and acetone; yield 0.09 g (31%), m.p. 180° C. (decomp.).

$^1$H NMR (DMSO-d$_6$): δ8.40 (H-4, H-6).
IR (KBr): 1735 cm$^{-1}$ ($\underline{CO}$-NHPyr).

EXAMPLE 11

1-N-Phenylcarbamoyl-5-bromopyrimidin-2-one

A mixture of 5-bromopyrimidin-2-one (1.0 mol) and phenyl isocyanate (4.6 mmol) in pyridine (1.0 ml) was stirred together at 50° C. for 2 h. The precipitate was collected and washed with ether and acetone; yield 0.13 g (44%), m.p. 200° C. (decomp.).

$^1$H NMR (DMSO-d$_6$): δ6.9–7.5 (Ph), 8.35 (H-4 and H-6).
IR (KBr): 1740 cm$^{-1}$ ($\underline{CO}$-NHPh).

EXAMPLE 12

1-(N-1-Naphthylcarbamoyl)-5-bromopyrimidin-2-one

A mixture of 5-bromopyrimidin-2-one (1.0 mmol) and 1-naphthyl isocyanate (1.5 mmol) in dry DMSO (1.0 ml) was stirred together at room temperature for 1.5 h before the precipitate was collected and washed with ether and acetone; yield 0.25 g (73%), m.p. 260° C.

$^1$H NMR (DMSO-d$_6$): δ7.3–8.3 (naphthyl), 8.39 (H-4, H-6), 9.13 (NH).

IR (KBr): 1740 cm$^{-1}$ (CO-NHNaph).

EXAMPLE 13

1-(N-1-Naphthylcarbamoyl)-5-trifluoromethyl-pyrimidin-2-one

A mixture of 5-trifluoromethylpyrimidin-2-one [see Preparation 11 in European Patent Publication No. 0056319 (Application No. 82300106.0)] (0.2 mmol) and 1-naphthylisocyanate (0.6 mmol) in dry DMSO (0.05 ml) was stirred together at 70° C. for 15 mins before ether was added (5 ml). The mixture was filtered, and the solid washed with acetone. The combined filtrate was cooled and the precipitate collected; yield 15 mg (23%) m.p. 140° C. (decomp).

pmr (DMSO, d6) δ7.3–8.3 (naphthyl), 9.05 (H-4, H-6).

IR (KBr) 1710 cm$^{-1}$ (CO)

EXAMPLE 14

1-(N-4-Trifluoromethylphenylcarbamoyl)-5-bromopyrimidin-2-one

A mixture of 5-bromopyrimidin-2-one (1 mmol) and 4-trifluoromethylphenyl isocyanate [see German OLS No. 1138391] (4 mmole) in pyridine (1 ml) was stirred and washed with ether, yield 0.23 g (62%), mp greater than 260° C. IR (KBr) 1735 cm$^{-1}$ (CO).

Pharmaceutical Composition Examples

Example A

| Injection solution | |
|---|---|
| 1. Active ingredient | 50 mg |
| 2. Polysorbate 80 | 2.50 mg |
| 3. Sodium chloride | 45 mg |
| 4. Water for injection | to 5.0 ml |

The sterile active ingredient, precipitated as a very fine powder, is dispersed aseptically in an aqueous vehicle containing the wetting agent (Polysorbate 80) and sufficient sodium chloride to produce an approximately isotonic solution this providing a suspension which may be used for deep intramuscular injection. Buffer salts may be incorporated (with a consequent reduction in the quantity of sodium chloride) to provide a suspension at the appropriate pH to ensure optimum stability of the compound before injection. The product may be presented as a dry filled vial of active ingredient together with a sterile ampoule of the remaining ingredients to permit extemporaneous preparation of the suspension immediately before injection.

Example B

| Injection solution | |
|---|---|
| 1. Active ingredient | 100 mg |
| 2. Aluminium monostearate | 5 mg |
| 3. Fractionated coconut oil | to 1 ml |

Sterile active ingredient in the form of a very fine powder is dispersed aseptically in a sterile oily vehicle containing a suspending agent whose structure is built up during the heat sterilisation of the vehicle. Such a product may be presented as a pre-prepared suspension for intra-muscular injection. The dose administered may be adjusted by alteration of the dose volume. The product may be presented in multidose vials and sealed with oil resistant rubber plugs to permit withdrawal of the required dose volume.

We claim:

1. A compound of the general formula:

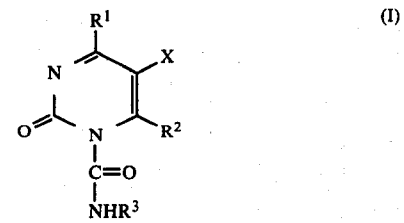

(wherein X represents a halogen atom or a trifluoromethyl group; $R^1$ and $R^2$, which may be the same or different, each represents a hydrogen atom or a $C_{1-4}$ alkyl group; and $R^3$ represents a hydrogen atom or a $C_{1-5}$ saturated or unsaturated straight or branched aliphatic group; a $C_{3-8}$ saturated or unsaturated cyclic aliphatic group; a $C_{1-4}$ aliphatic group carrying a 5- or 6-membered heterocyclic group having one heteroatom selected from oxygen, nitrogen and sulphur; an aralkyl group in which the alkyl portion contains 1 to 4 carbon atoms and in which the aryl portion contains up to 10 carbon atoms; a 5- or 6-membered heterocyclic group having one heteroatom selected from oxygen, nitrogen and sulphur; or a $C_{6-10}$ carbocyclic aryl group; any of said groups optionally carrying one or more substituents selected from halogen, oxo, hydroxy, mercapto, $C_{1-4}$ alkyl, $C_{1-4}$ alkoxy, $C_{1-4}$ alkanoyloxy and amino) and, where an acidic or basic group is present, the salts thereof.

2. A compound as claimed in claim 1 wherein $R^3$ represents a $C_{7-14}$ aralkyl group, a $C_{6-10}$ carbocyclic aryl group, a $C_{1-3}$ alkyl group carrying a 5- or 6-membered heterocyclic aryl group having one heteroatom selected from oxygen, nitrogen and sulphur, a 5- or 6-membered heterocyclic aryl group having one heteroatom selected from oxygen, nitrogen and sulphur or a $C_{1-5}$ alkyl or alkenyl group, said groups optionally carrying one or more substituents selected from $C_{1-4}$ alkyl and halogen.

3. A compound as claimed in claim 2 wherein $R^1$ and $R^2$ each represent a hydrogen atom and X represents a fluorine, chlorine, bromine or iodine atom.

4. A compound as claimed in claim 1 wherein $R^1$ and $R^2$ each represent a hydrogen atom.

5. A compound as claimed in claim 1 in which X represents a fluorine, chlorine bromine or iodine atom.

6. A compound as claimed in claim 1 which is: 1-N-Methylcarbamoyl-5-bromopyrimidin-2-one.

7. A compound as claimed in claim 1 which is: 1-N-Methylcarbamoyl-5-chloropyrimidin-2-one.

8. A pharmaceutical composition for combating abnormal cell proliferation comprising as active ingredient an effective amount of a compound of formula I as defined in claim 1 or, where an acidic or basic group is present, a physiologically compatible salt thereof, in association with a pharmaceutical carrier or excipient.

9. A method of combating abnormal cell proliferation in a host which comprises administering to said host an effective amount of a compound of formula I as defined in claim 1, or where an acidic or basic group is present, a physiologically compatible salt thereof.

* * * * *